United States Patent [19]
Gaudet

[11] Patent Number: 6,062,236
[45] Date of Patent: May 16, 2000

[54] DENTAL FLOSS HOLDER SYSTEM

[76] Inventor: Robert E. Gaudet, 162 Pratt Rd., Fitchburg, Mass. 01420

[21] Appl. No.: 09/339,799

[22] Filed: Jun. 24, 1999

[51] Int. Cl.[7] .................................................. A61C 15/00
[52] U.S. Cl. ............................................. 132/321; 206/49
[58] Field of Search .................................. 132/321, 323, 132/324; 206/368, 49, 63.5, 227; 229/87.05; 242/222, 587.2, 613.3

[56] References Cited

U.S. PATENT DOCUMENTS

| | | | |
|---|---|---|---|
| 1,273,894 | 7/1918 | Madison | 206/49 |
| 2,016,181 | 10/1935 | Sharp | 242/222 |
| 2,839,185 | 6/1958 | Isaacs | 206/49 |
| 3,092,251 | 6/1963 | Jaggers | 229/87.05 |
| 3,357,550 | 12/1967 | Holmes et al. | 242/613.3 |
| 3,803,650 | 4/1974 | D'Amico | 242/613.3 |
| 4,161,075 | 7/1979 | Eubanks et al. | 242/613.3 |
| 4,258,843 | 3/1981 | Wumer | 206/49 |
| 4,287,987 | 9/1981 | Hoffman et al. | 206/227 |
| 4,782,954 | 11/1988 | Reynolds | 206/227 |
| 4,972,946 | 11/1990 | Whittaker | 132/324 |
| 5,024,324 | 6/1991 | Whittaker | 206/49 |
| 5,074,100 | 12/1991 | Lepie | 132/321 |
| 5,678,580 | 10/1997 | Sherman | 132/324 |
| 5,819,919 | 10/1998 | O'Neal | 206/49 |

*Primary Examiner*—Todd E. Manahan

[57] ABSTRACT

A dental floss holder system for holding a single use sized length of dental floss in an easy to access and sanitary manner. The dental floss holder system includes a holder with an outer perimeter comprising a pair of end edges and a pair of side edges. An elongate flexible element is wrapped around the holder in a coil about the side edges of the holders. The flexible element has a pair of opposite ends. One of the ends of the flexible element is positioned towards one of the end edges of the holder and the other of the ends of the flexible element is positioned adjacent the other end edge of the holder. Each of the side edges of the holder has a notch therein. Each end of the flexible element is extended through the notch of the adjacent side edge such that aid notches hold end portions of the flexible element adjacent the ends of the flexible element to holder.

4 Claims, 2 Drawing Sheets

DENTAL FLOSS HOLDER SYSTEM

BACKGROUND OF THE INVENTION

1. Field of the Invention

The present invention relates to dental floss holders and more particularly pertains to a new dental floss holder system for holding a single use sized length of dental floss in an easy to access and sanitary manner.

2. Description of the Prior Art

The use of dental floss holders is known in the prior art. More specifically, dental floss holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,852,728; U.S. Pat. No. 4,712,572; U.S. Pat. No. Des. 291,412; U.S. Pat. No. 5,549,201; U.S. Pat. No. 5,249,674; and U.S. Pat. No. 4,693,365.

While these devices fulfill their respective, particular objectives and requirements, the aforementioned patents do not disclose a new dental floss holder system. The inventive device includes a holder with an outer perimeter comprising a pair of end edges and a pair of side edges. An elongate flexible element is wrapped around the holder in a coil about the side edges of the holders. The flexible element has a pair of opposite ends. One of the ends of the flexible element is positioned towards one of the end edges of the holder and the other of the ends of the flexible element is positioned adjacent the other end edge of the holder. Each of the side edges of the holder has a notch therein. Each end of the flexible element is extended through the notch of the adjacent side edge such that aid notches hold end portions of the flexible element adjacent the ends of the flexible element to holder.

In these respects, the dental floss holder system according to the present invention substantially departs from the conventional concepts and designs of the prior art, and in so doing provides an apparatus primarily developed for the purpose of holding a single use sized length of dental floss in an easy to access and sanitary manner.

SUMMARY OF THE INVENTION

In view of the foregoing disadvantages inherent in the known types of dental floss holders now present in the prior art, the present invention provides a new dental floss holder system construction wherein the same can be utilized for holding a single use sized length of dental floss in an easy to access and sanitary manner.

The general purpose of the present invention, which will be described subsequently in greater detail, is to provide a new dental floss holder system apparatus and method which has many of the advantages of the dental floss holders mentioned heretofore and many novel features that result in a new dental floss holder system which is not anticipated, rendered obvious, suggested, or even implied by any of the prior art dental floss holders, either alone or in any combination thereof.

To attain this, the present invention generally comprises a holder with an outer perimeter comprising a pair of end edges and a pair of side edges. An elongate flexible element is wrapped around the holder in a coil about the side edges of the holders. The flexible element has a pair of opposite ends. One of the ends of the flexible element is positioned towards one of the end edges of the holder and the other of the ends of the flexible element is positioned adjacent the other end edge of the holder. Each of the side edges of the holder has a notch therein. Each end of the flexible element is extended through the notch of the adjacent side edge such that aid notches hold end portions of the flexible element adjacent the ends of the flexible element to holder.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental floss holder system apparatus and method which has many of the advantages of the dental floss holders mentioned heretofore and many novel features that result in a new dental floss holder system which is not anticipated, rendered obvious, suggested, or even implied by any of the prior art dental floss holders, either alone or in any combination thereof.

It is another object of the present invention to provide a new dental floss holder system which may be easily and efficiently manufactured and marketed.

It is a further object of the present invention to provide a new dental floss holder system which is of a durable and reliable construction.

An even further object of the present invention is to provide a new dental floss holder system which is susceptible of a low cost of manufacture with regard to both materials and labor, and which accordingly is then susceptible of low prices of sale to the consuming public, thereby making such dental floss holder system economically available to the buying public.

Still yet another object of the present invention is to provide a new dental floss holder system which provides in the apparatuses and methods of the prior art some of the advantages thereof, while simultaneously overcoming some of the disadvantages normally associated therewith.

Still another object of the present invention is to provide a new dental floss holder system for holding a single use sized length of dental floss in an easy to access and sanitary manner.

Yet another object of the present invention is to provide a new dental floss holder system which includes a holder with an outer perimeter comprising a pair of end edges and a pair of side edges. An elongate flexible element is wrapped around the holder in a coil about the side edges of the holders. The flexible element has a pair of opposite ends. One of the ends of the flexible element is positioned towards one of the end edges of the holder and the other of the ends of the flexible element is positioned adjacent the other end edge of the holder. Each of the side edges of the holder has a notch therein. Each end of the flexible element is extended through the notch of the adjacent side edge such that aid notches hold end portions of the flexible element adjacent the ends of the flexible element to holder.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 4 thereof, a new dental floss holder system embodying the principles and concepts of the present invention will be described.

As best illustrated in FIGS. 1 through 4, the dental floss holder system generally comprises a holder with an outer perimeter comprising a pair of end edges and a pair of side edges. An elongate flexible element is wrapped around the holder in a coil about the side edges of the holders. The flexible element has a pair of opposite ends. One of the ends of the flexible element is positioned towards one of the end edges of the holder and the other of the ends of the flexible element is positioned adjacent the other end edge of the holder. Each of the side edges of the holder has a notch therein. Each end of the flexible element is extended through the notch of the adjacent side edge such that aid notches hold end portions of the flexible element adjacent the ends of the flexible element to holder.

Figure 3:
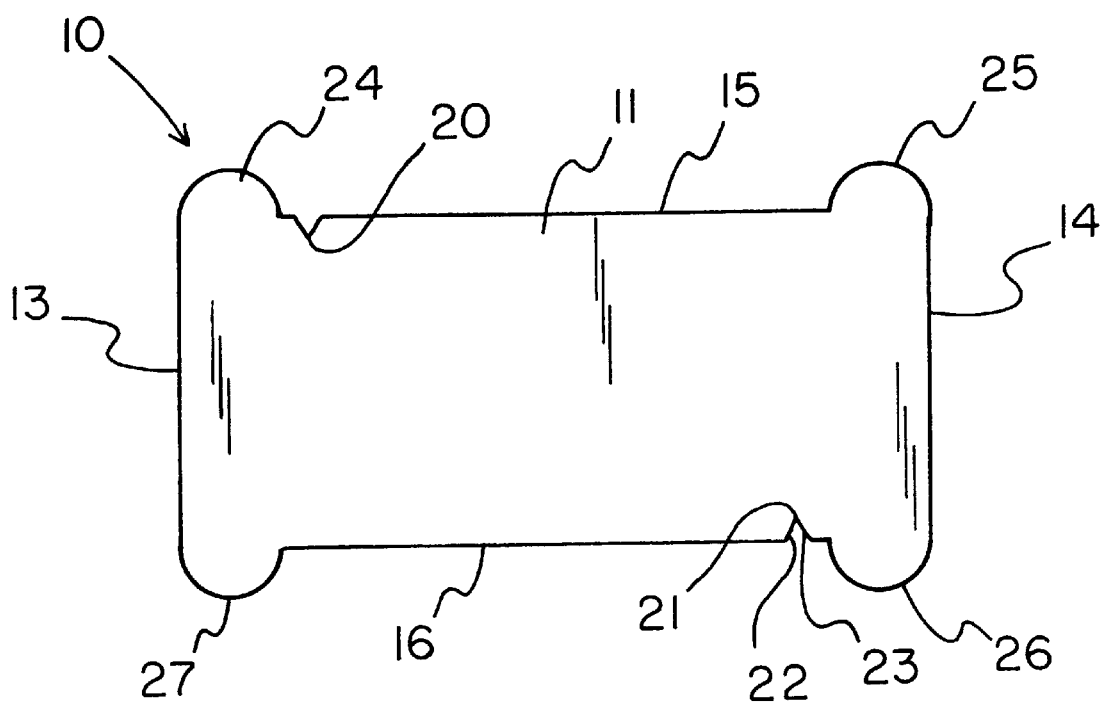
FIG. 3 is a schematic plan view of the holder.

Specifically, the dental floss holder system includes a substantially planar holder 10 having a pair of substantially planar faces 11,12 and an outer perimeter comprises a pair of end edges 13,14 and a pair of side edges 15,16. The holder may comprise a cardboard paper material or even a plastic cardstock material or a combination thereof. With reference to FIG. 3, the planar holder may have a generally rectangular configuration so that the end edges of the holder are extended substantially parallel to each other and that the side edges of the holder are extended substantially parallel to each other and substantially perpendicular to the end edges of the holder.

An elongate flexible element 17 comprising dental floss is wrapped around the holder in a coil about the side edges of the holders. In one embodiment, the coil should have at least ten turns around the holder. In one illustrative embodiment, the flexible element may have a length of about 24 inches which is sufficient for a single flossing of all of the user's teeth.

The flexible element has a pair of opposite ends 18,19. One of the ends of the flexible element is positioned adjacent side edges towards one of the end edges of the holder and the other of the ends of the flexible element is positioned adjacent the other side edge towards the other end edge of the holder.

Figures 2, 4:
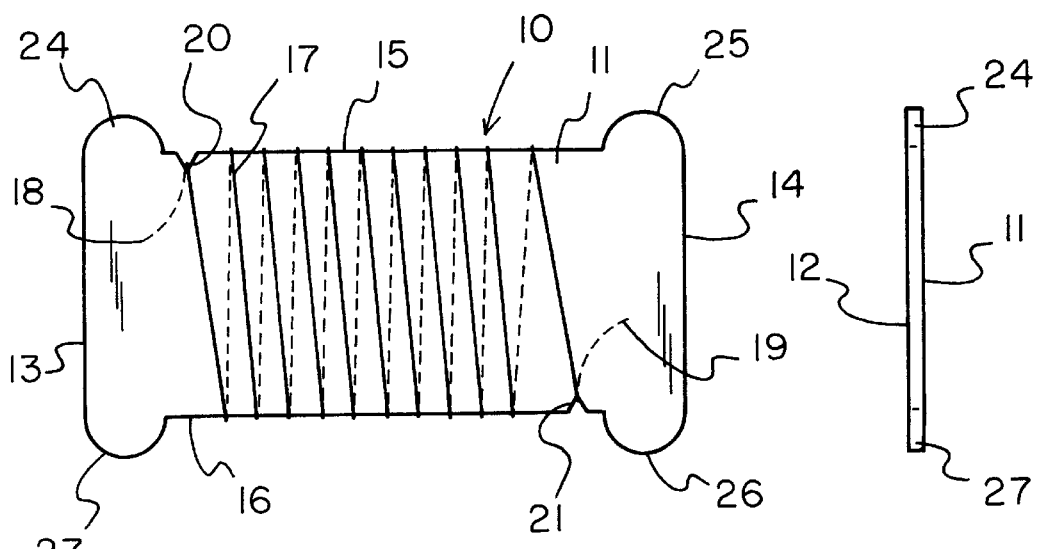
FIG. 2 is a schematic plan view of the holder with the flexible element coiled therearound.
FIG. 4 is a schematic end view of the holder.

Each of the side edges of the holder has a notch 20,21 therein. The notch of one of the side edges may be positioned towards one end edge of the holder and the notch of the other of the side edges may be positioned towards the other end edge of the holder. As illustrated in FIG. 2, each end of the flexible element is extended through the notch of the side edge located adjacent to the respective end of the flexible element. This way, the notches hold end portions of the flexible element adjacent the ends of the flexible element to holder.

In an embodiment of the holder, each notch may be generally V-shaped with a pair of peripheral edges 22,23 extending at an acute angle to one another. In one illustrative embodiment, the acute angle between the pair of peripheral edges of each notch may be about 60 degrees. The acute angle forms a vertex which is helpful in holding the end portions of the flexible element in their respective notches.

Each of the sides edges of the holder may have a spaced apart pair of tabs 24,25,26,27 outwardly extending therefrom. In such an embodiment, the notches of the side edges are positioned between the tabs of the adjacent side edges of the holder. In use, the tabs are designed for providing locations for a user to grasp the holders with their fingertips so that the user is only touching the holder around the outer perimeter of the holder to thereby prevent a user from contaminating the floss wrapped around the holder. Additionally, the tabs are also designed for providing stops for helping prevent the floss from sliding off of the ends of the holder.

In one such embodiment, the tabs each may have a generally semi-circular rounded outer perimeter with a convexity facing outwards from the adjacent side edge. In use, the rounded outer perimeter is designed for helping to prevent injury to the fingers of the user grasping the tabs by eliminating sharp corners which could get underneath the fingernails of the user and thereby cause injury to the user's fingers. In one possible version of this embodiment, the tabs may have substantially equal radii.

One tab of each side edge may be positioned adjacent one of the end edges of the holder and the other tab of each side edge may be positioned adjacent the other of the end edges of the holder. In such an embodiment, each of the end edges of the holder may be extended tangentially to the outer perimeters of the adjacent tabs.

The holder has a length defined between the end edges and a width defined between the side edges. Typically, the width of the holder may be about one-half the length of the holder. In one illustrative embodiment, the length of the holder may be between about ¾ inch and about 2 inches and the width of the holder may be between about ⅜ inch and about 1 inch. In a particular illustrative embodiment of this range, the length of the holder may be about ¾ inch and the width of the holder may be about ⅜ inch. In this embodiment, the radius of each tab may be about 1/16 inch.

Figure 1:
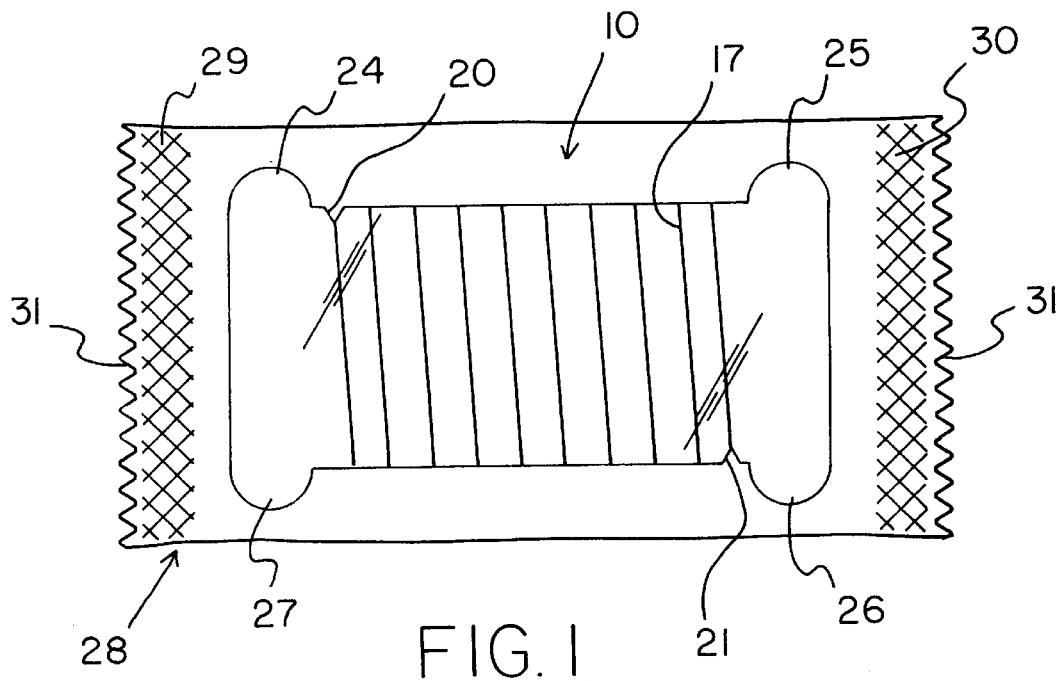
FIG. 1 is a schematic plan view of an embodiment of the dental floss holder system according to the present invention.

The system may also include a packet 28 substantially enclosing the holder and flexible element therein as illustrated in FIG. 1. The packet may comprise a tearable sheet material such as a plastic or cellophane sheet material which is easily torn. The packet may also comprises a translucent or transparent material to permit viewing of the holder and flexible element therein.

The packet may have a pair of heat sealed ends 29,30 with each of the ends of the packet having a serrated edge 31 comprising a plurality of generally triangular serrations. In use, the serrations are designed for providing loci for a user to more easily initiate a tear in the packet to open the packet.

In use, the packet is torn open and the holder with the flexible element coiled therearound are removed from the packet The flexible element is then uncoiled from the holder and used to floss the user's teeth. After flossing, the packet, the holder, and the flexible element may all be disposed of.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A single use disposable dental floss holder system, comprising:

a substantially planar holder having a pair of substantially planar faces and an outer perimeter comprising a pair of end edges and a pair of side edges, said holder comprising a plastic cardstock material;

an elongate flexible element being wrapped around said holder in a coil about said side edges of said holders, said coil having at least ten turns around said holder;

said planar holder having a generally rectangular configuration, said end edges of said holder being extended substantially parallel to each other, said side edges of said holder being extended substantially parallel to each other and substantially perpendicular to said end edges of said holder;

each of said sides edges of said holder having a spaced apart pair of tabs outwardly extending therefrom, said tabs providing locations for a user to grasp the holder with fingertips so that the user is only touching the holder around the outer perimeter of the holder to thereby reduce contamination by the user's fingertips of an elongate flexible element wrapped about said holder, said tabs providing stops for helping prevent the elongate flexible element from sliding off of the ends of the holder;

said tabs each having a generally semi-circular rounded outer perimeter with a convexity facing outwards from the adjacent side edge;

said tabs having substantially equal radii;

one tab of each side edge being positioned adjacent one of said end edges of said holder, the other tab of each side edge being positioned adjacent the other of said end edges of said holder;

each of said end edges of said holder being extended tangentially to the outer perimeters of the adjacent tabs;

said holder having a length defined between said end edges and a width defined between said side edges;

said length of said holder between about ¾ inch and about 2 inches and said width of said holder is between about ⅜ inch and about 1 inch:

wherein said width of said holder is about one-half said length of said holder;

said flexible element having a pair of opposite ends defining a length, wherein the length of said flexible element is about 24 inches which is sufficient for a single flossing of all of the user's teeth;

one of said ends of said flexible element being positioned towards one of said end edges of said holder and the other of said ends of said flexible element being positioned adjacent the other end edge of said holder;

each of said side edges of said holder having a notch therein;

said notch of one of said side edges being positioned towards one end edge of said holder, said notch of the other of said side edges being positioned towards the other end edge of said holder;

said notches of said side edges being positioned between said tabs of the adjacent side edges of said holder;

each end of said flexible element being extended through the notch of the side edge located adjacent to the respective end of said flexible element, said notches holding end portions of said flexible element adjacent said ends of said flexible element to holder;

each notch being generally V-shaped and having a pair of peripheral edges extending at an acute angle to one another;

a packet substantially enclosing said holder and flexible element therein;

said packet comprising a tearable sheet material:

said packet comprising a translucent material; and said packet having a pair of heat sealed ends, each of said ends of said packet having a serrated edge comprising a plurality of generally triangular serrations, said serrations being adapted for providing loci for a user to more easily initiate a tear in the packet to open the packet.

2. The dental floss holder system of claim 1, wherein said length of said holder is about ¾ inch and said width of said holder is about ⅜ inch, and said radius of each tab is about 1/16 inch.

3. The dental floss holder system of claim 1, wherein said packet comprises a transparent material to permit viewing of the holder and flexible element therein.

4. The dental floss holder system of claim 1, wherein said packet comprises a plastic sheet material.

* * * * *